(12) United States Patent
Trout, III et al.

(10) Patent No.: US 7,101,366 B2
(45) Date of Patent: Sep. 5, 2006

(54) APPARATUS AND METHOD FOR PERFORMING A SURGICAL PROCEDURE

(75) Inventors: Hugh Trout, III, Bethesda, MD (US); Howard Tanner, Logan, UT (US); Frank Patterson, Exeter, NH (US)

(73) Assignee: Eva Corporation

( * ) Notice: Subject to any disclaimer, the term of this patent is extended or adjusted under 35 U.S.C. 154(b) by 52 days.

(21) Appl. No.: 10/411,135

(22) Filed: Apr. 11, 2003

(65) Prior Publication Data

US 2004/0002679 A1    Jan. 1, 2004

Related U.S. Application Data

(63) Continuation-in-part of application No. 09/783,313, filed on Feb. 15, 2001, now Pat. No. 6,607,555.

(60) Provisional application No. 60/371,500, filed on Apr. 11, 2002, provisional application No. 60/182,543, filed on Feb. 15, 2000.

(51) Int. Cl.
*A61B 18/20* (2006.01)
*A61B 18/24* (2006.01)
*A61B 17/12* (2006.01)

(52) U.S. Cl. .......... 606/15; 606/153; 606/158; 623/1.23

(58) Field of Classification Search ........ 606/7, 606/15, 153–158; 623/1.11, 1.14
See application file for complete search history.

(56) References Cited

U.S. PATENT DOCUMENTS

| | | | |
|---|---|---|---|
| 4,562,596 A | 1/1986 | Kornberg | |
| 4,787,899 A | 11/1988 | Lazarus | |
| 4,917,084 A | 4/1990 | Sinofsky | |
| 5,042,707 A | 8/1991 | Taheri | |
| 5,147,354 A | 9/1992 | Boutacoff et al. | |
| 5,254,112 A | 10/1993 | Sinofsky et al. | |
| 5,891,133 A * | 4/1999 | Murphy-Chutorian | 606/7 |
| 5,938,696 A * | 8/1999 | Goicoechea et al. | 606/194 |
| 5,957,940 A * | 9/1999 | Tanner et al. | 606/155 |
| 5,997,556 A * | 12/1999 | Tanner | 606/153 |
| 6,113,588 A * | 9/2000 | Duhaylongsod et al. | 606/15 |
| 6,607,555 B1* | 8/2003 | Patterson et al. | 623/1.23 |
| 2004/0098043 A1* | 5/2004 | Trout, III | 606/213 |

* cited by examiner

*Primary Examiner*—A. Farah
(74) *Attorney, Agent, or Firm*—John N. Coulby; Kelley Drye; Collier Shannon

(57) ABSTRACT

An embodiment of the present invention relates to methods for performing a surgical procedure. In particular, an embodiment of the present invention is directed to methods for performing a surgical procedure, using a delivery catheter containing a laser fiber assembly. In accordance with an embodiment of the present invention, a method of performing a surgical procedure comprises the steps of: advancing a delivery catheter to a procedure specific area; activating a laser fiber assembly disposed within the delivery catheter; and advancing the laser fiber assembly to create a treatment specific hole at the procedure specific area.

11 Claims, 13 Drawing Sheets

APPARATUS AND METHOD FOR PERFORMING A SURGICAL PROCEDURE

CROSS-REFERENCE TO RELATED APPLICATIONS

The present application is a continuation-in-part of, and is entitled to the benefit of the earlier filing date and priority of, U.S. Non-Provisional application Ser. No. 09/783,313, filed on Feb. 15, 2001, now U.S. Pat. No. 6,607,555, which is entitled to the benefit of the earlier filing date and priority of U.S. Provisional Application Ser. No. 60/182,543, filed on Feb. 15, 2000. An embodiment of the present invention relates to, and is entitled to the benefit of the earlier filing date and priority of U.S. Provisional Application Ser. No. 60/371,500, filed on Apr. 11, 2002.

FIELD OF THE INVENTION

An embodiment of the present invention relates to methods for performing a surgical procedure. In particular, an embodiment of the present invention is directed to methods for performing a surgical procedure, such as but not limited to repairing an aneurysm, using a delivery catheter having a laser fiber assembly.

BACKGROUND OF THE INVENTION

An aneurysm is a ballooning of the wall of an artery resulting from the weakening of the artery due to disease or other conditions. Left untreated, the aneurysm will frequently rupture, resulting in loss of blood through the rupture and death.

Aortic aneurysms are the most common form of arterial aneurysm and are life threatening. The aorta is the main artery which supplies blood to the circulatory system. The aorta arises from the left ventricle of the heart, passes upward and bends over behind the heart, and passes down through the thorax and abdomen. Among other arterial vessels branching off the aorta along its path, the abdominal aorta supplies two side vessels to the kidneys, the renal arteries. Below the level of the renal arteries, the abdominal aorta continues to about the level of the fourth lumbar vertebrae (or the navel), where it divides into the iliac arteries. The iliac arteries, in turn, supply blood to the lower extremities and perineal region.

It is common for an aortic aneurysm to occur in that portion of the abdominal aorta between the renal arteries and the iliac arteries. This portion of the abdominal aorta is particularly susceptible to weakening, resulting in an aortic aneurysm. Such an aneurysm is often located near the iliac arteries. An aortic aneurysm larger than about 5 cm in diameter in this section of the aorta is ominous. Left untreated, the aneurysm may rupture, resulting in rapid, and usually fatal, hemorrhaging. Typically, a surgical procedure is not performed on aneurysms smaller than 5 cm because no statistical benefit exists in performing such procedures.

Aneurysms in the abdominal aorta are associated with a particularly high mortality rate; accordingly, current medical standards call for urgent operative repair. Abdominal surgery, however, results in substantial stress to the body. Although the mortality rate for an aortic aneurysm is high, there is also considerable mortality and morbidity associated with open surgical intervention to repair an aortic aneurysm. This intervention involves penetrating the abdominal wall to the location of the aneurysm to reinforce or replace the diseased section of the aortic aneurysm. A prosthetic device, typically a synthetic tube graft, is used for this purpose. The graft serves to exclude the aneurysm from the circulatory system, thus relieving pressure and stress on the weakened section of the aorta at the aneurysm.

Repair of an aortic aneurysm by surgical means is a major operative procedure. Substantial morbidity accompanies the procedure, resulting in a protracted recovery period. Further, the procedure entails a substantial risk of mortality. While surgical intervention may be indicated and the surgery carries attendant risk, certain patients may not be able to tolerate the stress of intra-abdominal surgery. It is, therefore, desirable to reduce the mortality and morbidity associated with intra-abdominal surgical intervention.

In recent years, methods have been developed to attempt to treat an aortic aneurysm without the attendant risks of intra-abdominal surgical intervention. Among them are inventions disclosed and claimed in Kornberg, U.S. Pat. No. 4,562,596 for Aortic Graft, Device and Method for Performing an Intraluminal Abdominal Aortic Aneurysm Repair; Lazarus, U.S. Pat. No. 4,787,899 for Intraluminal Graft Device, System and Method; and Taheri, U.S. Pat. No. 5,042,707 for Intravascular Stapler, and Method of Operating Same.

Although in recent years certain techniques have been developed that may reduce the stress, morbidity, and risk of mortality associated with surgical intervention to repair aortic aneurysms, none of the systems that have been developed effectively treat the aneurysm and exclude the affected section of aorta from the pressures and stresses associated with circulation. None of the devices disclosed in the references provide a reliable and quick means to reinforce an aneurysmal artery. In addition, all of the prior references require a sufficiently large section of healthy aorta surrounding the aneurysm to ensure attachment of the graft. The neck of the aorta at the cephalad end (i.e., above the aneurysm) is usually sufficient to maintain a graft's attachment means. However, when an aneurysm is located near the iliac arteries, there may be an ill-defined neck or no neck below the aneurysm. Such an ill-defined neck would have an insufficient amount of healthy aortic tissue to which to successfully mount a graft. Furthermore, much of the abdominal aorta wall may be calcified which may make it extremely difficult to attach the graft to the wall. Furthermore, the prior art does not disclose surgical devices that can be used during a surgical procedure that address these concerns. Others have developed devices that are not easily manipulated or oriented during intraluminal surgical procedures.

Methods have also been developed to use lasers to perform certain surgical procedures, particularly, Boutacoff et al., U.S. Pat. No. 5,147,354 for Mid-Infrared Laser Endoscope (hereinafter "Boutacoff"). Boutacoff is directed to a Holmium YAG ("Ho:YAG") laser coupled to a needle tip through a flexible, fiber optical cable for performing endoscopic and arthroscopic surgery. Boutacoff only discloses use of laser energy during arthroscopic and endoscopic procedures. An embodiment of the present invention, in contrast, is directed to catheter-based surgical procedures. In arthroscopic and endoscopic procedures, tissue is ablated for the purpose of removing excess tissue. The tissue must be distended by gas or fluids to prevent burning or smoking during the procedure. In Boutacoff, a fluid field is maintained to flush the knee, thereby reducing the amount of smoke produced by the ablation procedure. The fluid field is necessary to distend the tissue and to improve visualization during the procedure.

In contrast, an embodiment of the present invention is not directed to ablating tissue with laser energy, but rather to penetrating tissue or other components to create treatment specific holes therein. Because tissue is not ablated or removed as in Boutacoff, burning and smoking are not problems, and thus, there is no need to maintain a fluid field. Hence, an embodiment of the present invention is not limited and possesses none of the needs of Boutacoff, mainly ablation for removing excess tissue and maintenance of a fluid field. Rather, an embodiment of the present invention is a novel application of laser technology for the performance of surgical procedures.

It is an advantage of an embodiment of the present invention to provide a method for creating a treatment specific hole at a procedure specific area with a laser fiber assembly. It is another advantage of an embodiment of the present invention to provide a method for repairing tissue by creating a treatment specific hole in the tissue with a laser fiber assembly and inserting a fastener through the hole. It is yet another advantage of an embodiment of the present invention to provide a method for repairing an aneurysm by creating a treatment specific hole in a surgical component and a vessel wall with a laser fiber assembly and inserting a fastener through the hole.

Additional advantages of embodiments of the invention are set forth, in part, in the description that follows and, in part, will be apparent to one of ordinary skill in the art from the description and/or from the practice of the invention.

SUMMARY OF THE INVENTION

Responsive to the foregoing challenges, Applicant has developed an innovative method of performing a surgical procedure, comprising the steps of: advancing a delivery catheter to a procedure specific area; activating a laser fiber assembly located within the delivery catheter; and advancing the laser fiber assembly to create a treatment specific hole at the procedure specific area. The laser fiber assembly may comprise an optical fiber and a Holmium YAG ("Ho:YAG") laser, or any other suitable fiber and laser combination. The method may further comprise the step of extending the sheath of the delivery catheter prior to activating the laser fiber assembly, wherein an end portion of the sheath assumes an angular configuration.

According to an alternative embodiment of the present invention, the method of performing a surgical procedure other than arthroscopy and endoscopy, comprising the steps of: advancing a delivery catheter to a procedure specific area; activating a laser fiber assembly disposed within the delivery catheter; and advancing the laser fiber assembly to create a treatment specific hole at the procedure specific area.

In another alternative embodiment of the present invention, the method of performing a surgical procedure, comprising the steps of: advancing a delivery catheter to a procedure specific area; activating a laser fiber assembly disposed within the delivery catheter, wherein at least one fastener is positioned at the distal portion of the laser fiber assembly; advancing the laser fiber assembly and the at least one fastener through at least one material at the procedure specific area to create a treatment specific hole in at least one material; and retracting the laser fiber assembly such that the at least one fastener remains inserted in the at least one material.

According to yet another embodiment of the present invention, the method of performing a surgical procedure, comprising the steps of: advancing a delivery catheter through a vessel to a procedure specific area within the vessel; activating a laser fiber assembly disposed within the delivery catheter, wherein at least one fastener is positioned at a distal portion of the laser fiber assembly; advancing the laser fiber assembly and the fastener through a surgical component and the vessel to create a treatment specific hole in the surgical component and the vessel through which the fastener extends; and retracting the laser fiber assembly such that the at least one fastener remains attached to the surgical component and the vessel.

According to yet another alternative embodiment of the present invention, the method of performing a surgical procedure, comprising the steps of: advancing a delivery catheter through a vessel to a procedure specific area within a vessel; extending the delivery catheter such that an inner sheath of the delivery catheter extends from the delivery catheter, wherein an end portion of the inner sheath assumes an angular configuration; advancing the inner sheath from within the delivery catheter such that the delivery catheter contacts a surgical component at a location opposite to a point of contact of the inner sheath; further advancing the inner sheath such that the inner sheath contacts the surgical component; activating a laser fiber assembly disposed within the inner sheath, wherein at least one fastener is positioned at a distal portion of the laser fiber assembly; advancing the laser fiber assembly and the at least one fastener through the surgical component and the vessel to create a treatment specific hole in the surgical component and the vessel through which the fastener extends; and retracting the laser fiber assembly and the inner sheath such that the at least one fastener remains attached to the surgical component and the vessel.

It will be apparent to those skilled in the art that variations and modifications embodying the present invention can be made without departing from the scope or spirit of the invention. For example, the delivery catheter may be advanced to the procedure specific area within an introducer sheath and may extend from within the introducer sheath. The delivery catheter may comprise an inner sheath and an outer sheath, wherein the outer sheath assumes an angular configuration and the inner sheath is advanced from within the outer sheath. In addition, the laser fiber assembly may be located within the inner sheath. Thus, it is intended that embodiments of the present invention cover all such modifications and variations of the invention, provided they come within the scope of the appended claims and their equivalents.

It also is to be understood that both the foregoing general description and the following detailed description are exemplary and explanatory only, and are not restrictive of the invention as claimed. The accompanying drawings, which are incorporated herein by reference, and which constitute a part of this specification, illustrate certain embodiments of the invention and, together with the detailed description, serve to explain the principles of the present invention.

BRIEF DESCRIPTION OF THE DRAWINGS

In order to assist the understanding of this invention, reference will now be made to the appended drawings, in which like reference characters refer to like elements. The drawings are exemplary only, and should not be construed as limiting the invention.

DETAILED DESCRIPTION OF EMBODIMENTS OF THE INVENTION

Figure 1:
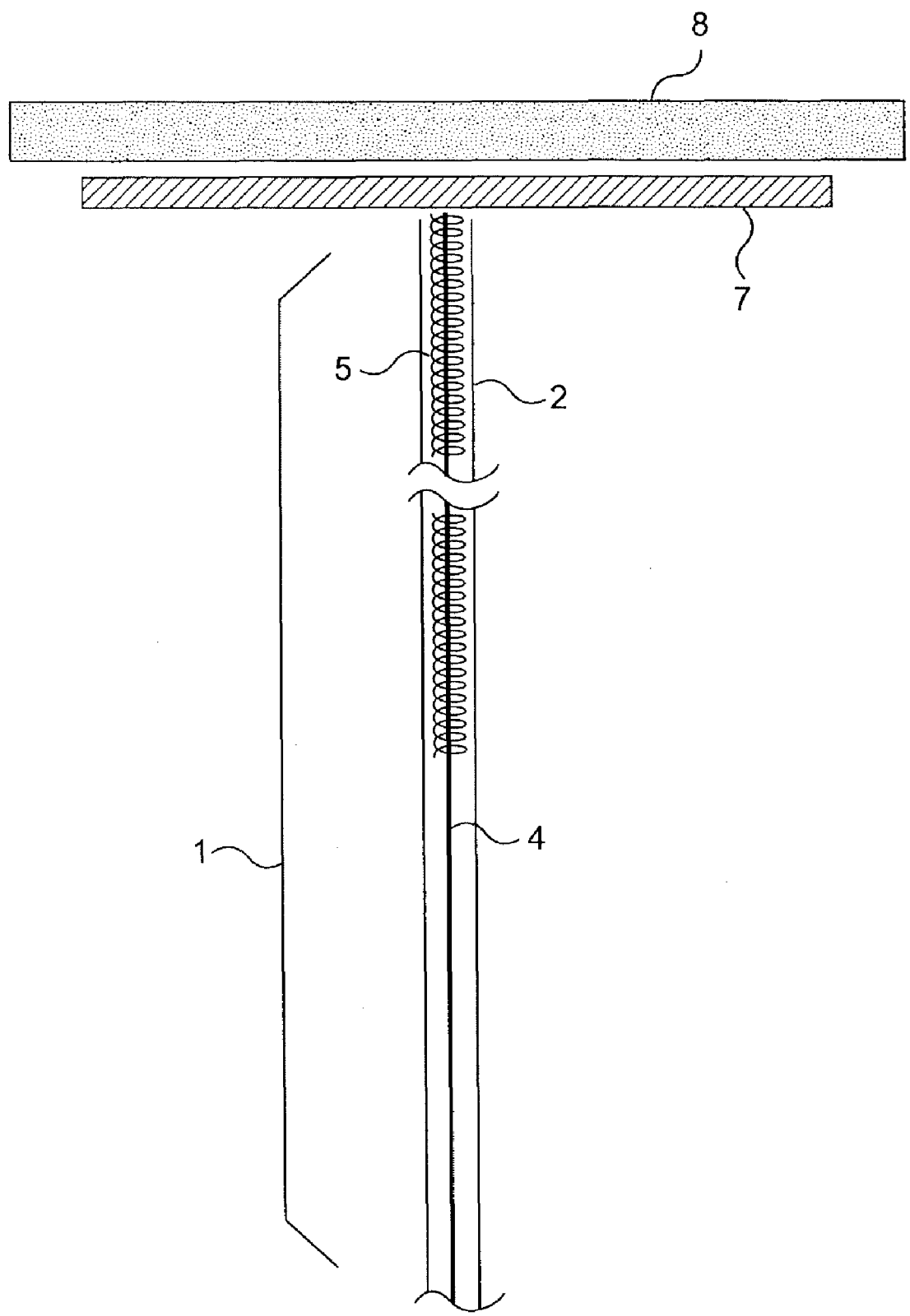
FIGS. 1 through 4 are perspective views of a delivery catheter advanced to a procedure specific area in accordance with an embodiment of the present invention.
Figure 2:
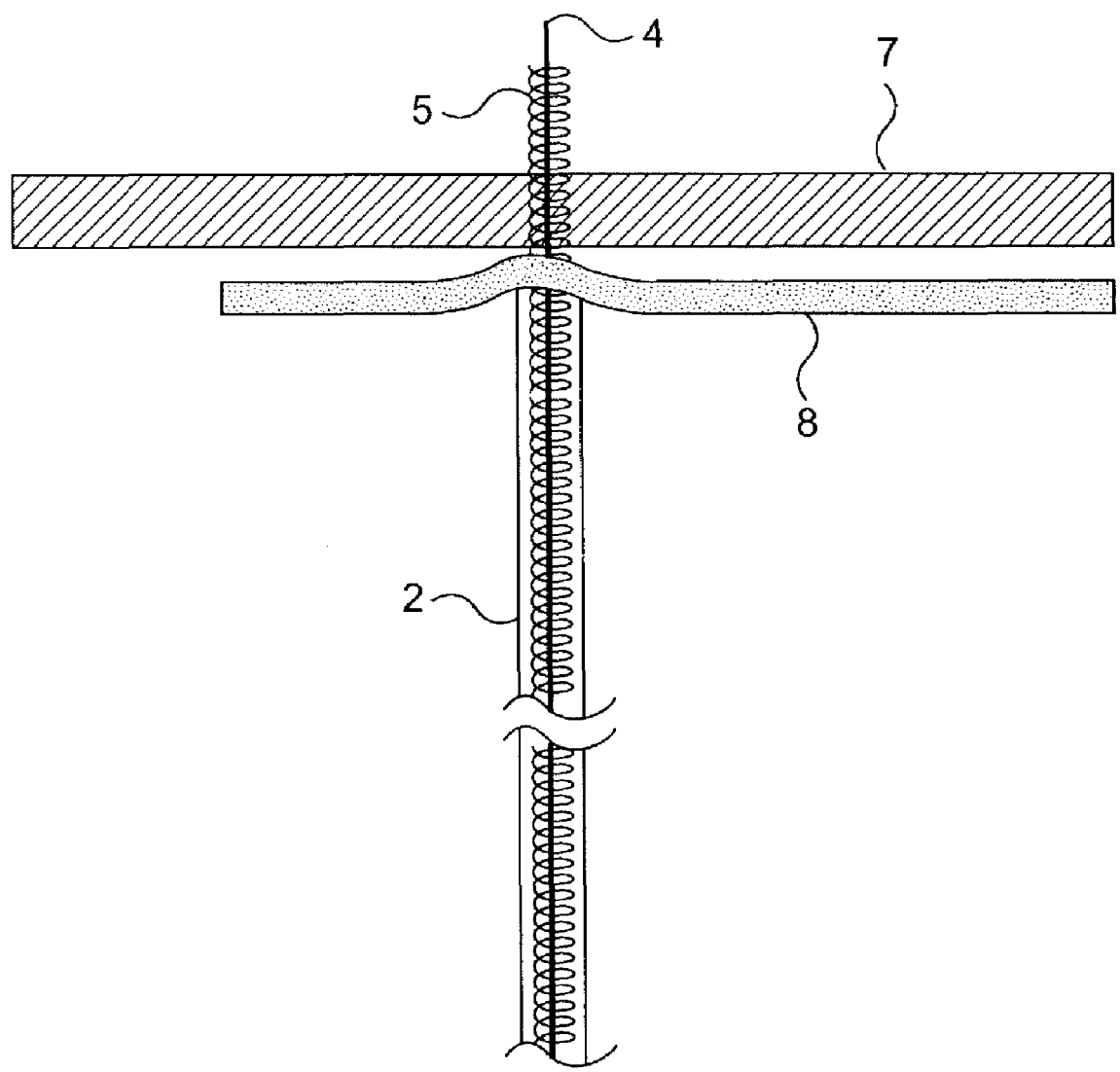
Figure 3:
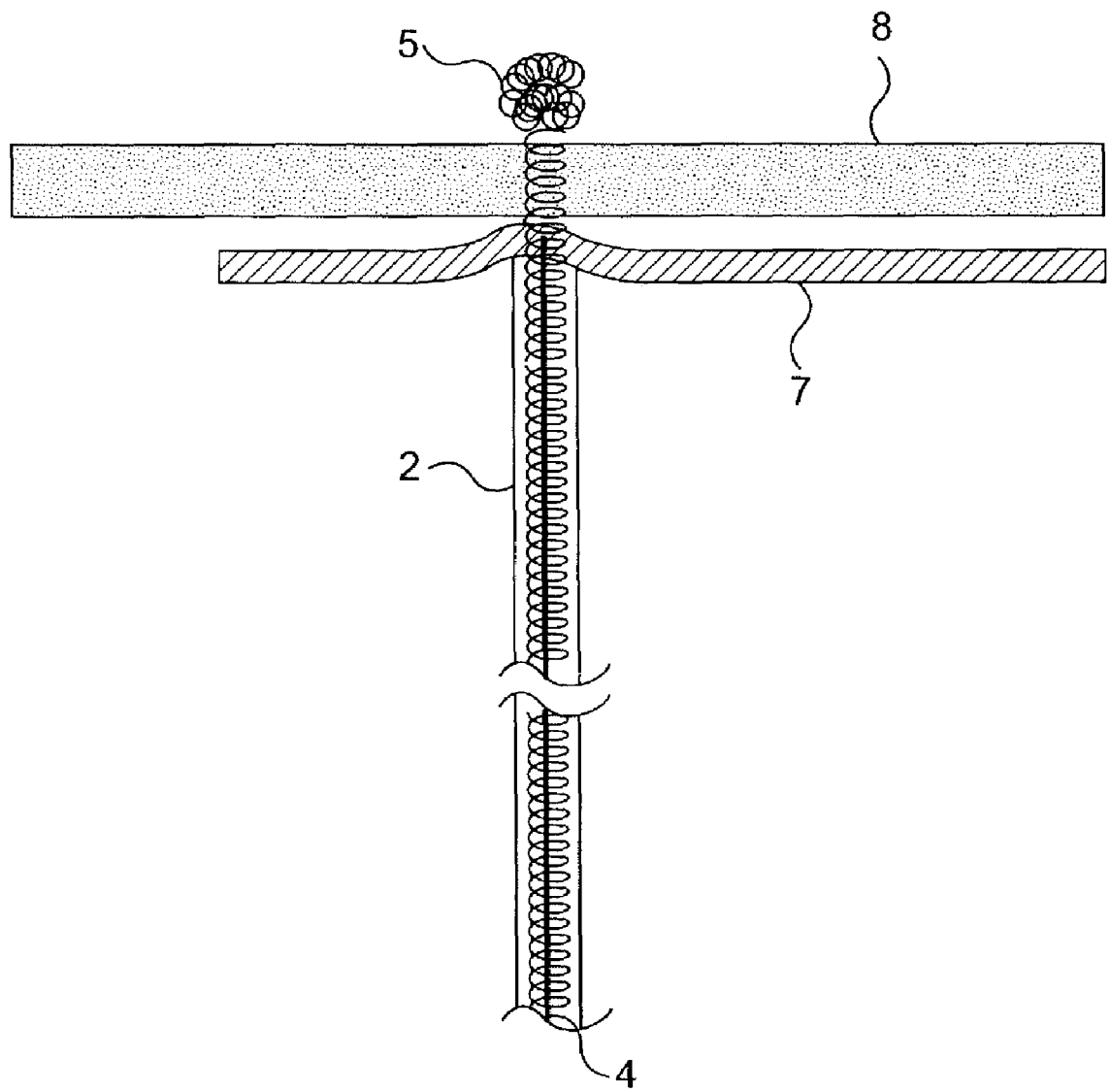
Figure 4:
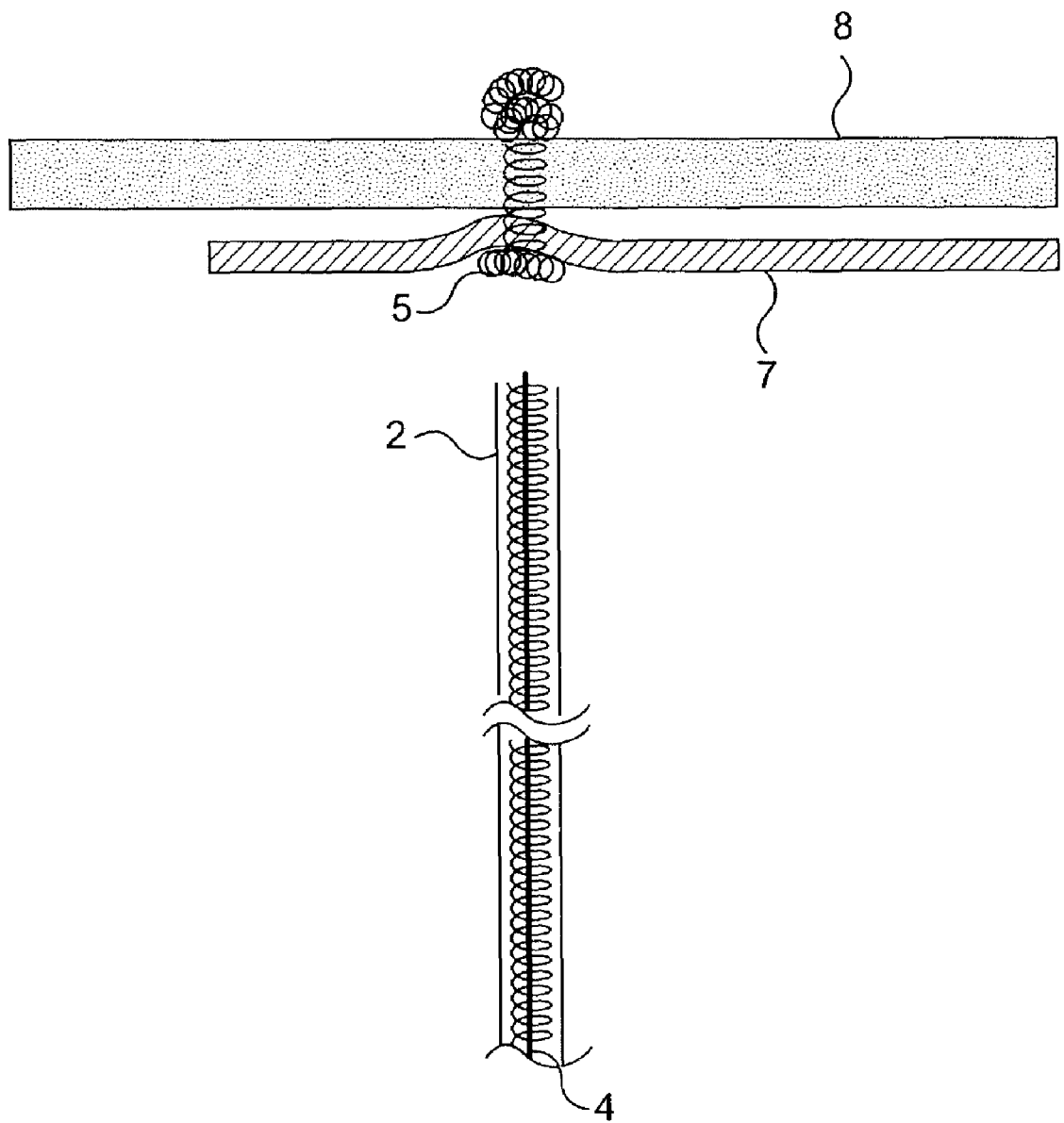
Figure 5:
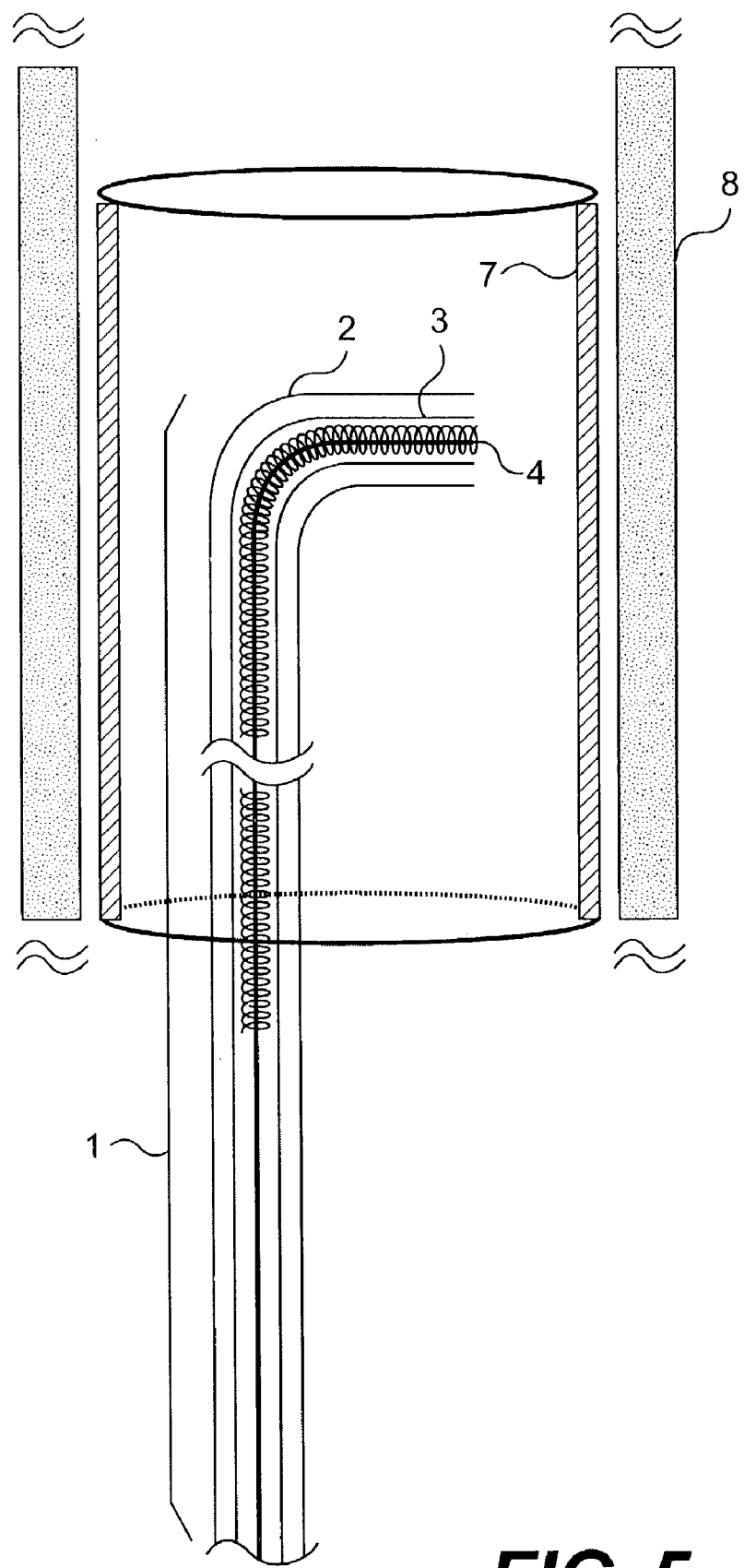
FIG. 5 is a perspective view of a delivery catheter at a procedure specific area in a vessel, wherein an outer sheath of the catheter is extended such that it assumes an angular configuration, in accordance with an embodiment of the present invention.

Reference will now be made in detail to embodiments of the present invention, examples of which are illustrated in the accompanying drawings. FIGS. 1 through 4 depict an embodiment of the present invention. In FIG. 1, the delivery catheter 1 is comprised of an outer sheath 2. The delivery catheter 1 advances through a vessel (not shown) to a procedure specific area within the vessel. The advancement of the delivery catheter 1 is through, but not limited to, the extension of the delivery catheter 1 by a mechanical mechanism or by hand or by any other suitable means. A laser fiber assembly 4 is located with an outer sheath 2 of the delivery catheter 1, wherein at least one fastener 5 may be positioned in conjunction with the laser fiber assembly 4. At least one fastener 5 may also be positioned within a hollow laser fiber assembly 4 (not shown). In FIG. 2, the laser fiber assembly 4 is activated. The laser fiber assembly 4 and the fastener 5 advances, either simultaneously or in sequence through a surgical component 7 and the vessel wall 8 to create a treatment specific hole in the surgical component 7 and the vessel wall 8 through which the fastener 5 extends. The activation of the laser fiber assembly 4 occurs by, but is not limited to, mechanical or electrical mechanisms, or any other appropriate mechanism. The laser fiber assembly 4 may also be replaced by a piezoelectric assembly (not shown). In FIGS. 3 and 4, the laser fiber assembly 4 and the outer sheath 2 are retracted such that the fastener 5 secures the surgical component 7 to the vessel wall 8. The laser fiber assembly 4 may comprise a Ho:YAG laser a Ho:YLF laser, a laser with a wavelength between 1.8 and 2.21μ or any other suitable laser. In a further embodiment, the outer sheath 2 of the delivery catheter 1 is articulatable wherein an end portion of the outer sheath 2 assumes an angular configuration, as illustrated in FIG. 5. In yet a further embodiment, an expandable member such as, but not limited to, a balloon, or additional articulation of the delivery catheter to create an appositional force, or any other suitable means may be used in conjunction with the outer sheath 2 (not shown).

The fastener 5 is a flexible fastener that applies a force to secure the surgical component to the vessel, as disclosed in the following U.S. patent applications: U.S. Provisional Patent Application No. 60/181,230, filed Feb. 9, 2000; U.S. patent application Ser. No. 09/442,768, filed Nov. 18, 1999; U.S. patent application Ser. No. 09/213,233, filed Dec. 17, 1998, now U.S. Pat. No. 5,997,556; U.S. patent application Ser. No. 08/958,524, filed Oct. 27, 1997, now U.S. Pat. No. 5,957,940, U.S. patent application Ser. No. 08/896,415, filed Jul. 18, 1997, now U.S. Pat. No. 5,944,750; and U.S. Provisional Patent Application No. 60/051,209, filed Jun. 30, 1997. The subject matter of these patent applications is incorporated herein specifically by reference, in their entirety.

Another embodiment of the present invention is depicted in FIGS. 5 through 9. As illustrated in FIG. 5, the delivery catheter 1, which comprises an outer sheath 2 and an inner sheath 3, is advanced within the vessel to a procedure specific area. The delivery catheter 1 may be advanced through the lumen of a surgical component 7, such as, but not limited to, a prosthetic graft, which is positioned adjacent to the vessel wall 8. The outer sheath 2 of the delivery catheter 1 is extended such that the end portion of the outer sheath 2 assumes an angular configuration, as depicted in FIG. 5. In a further embodiment, the angular configuration may be achieved by manipulating at least one pull wire extending through the outer sheath 2 and exiting the outer sheath 2 at a point outside the body of the patient. The pull wire may also be located on the exterior of the outer sheath 2. The end portion of the outer sheath 2 may be deflected when the pull wire is tensioned.

Figure 6:
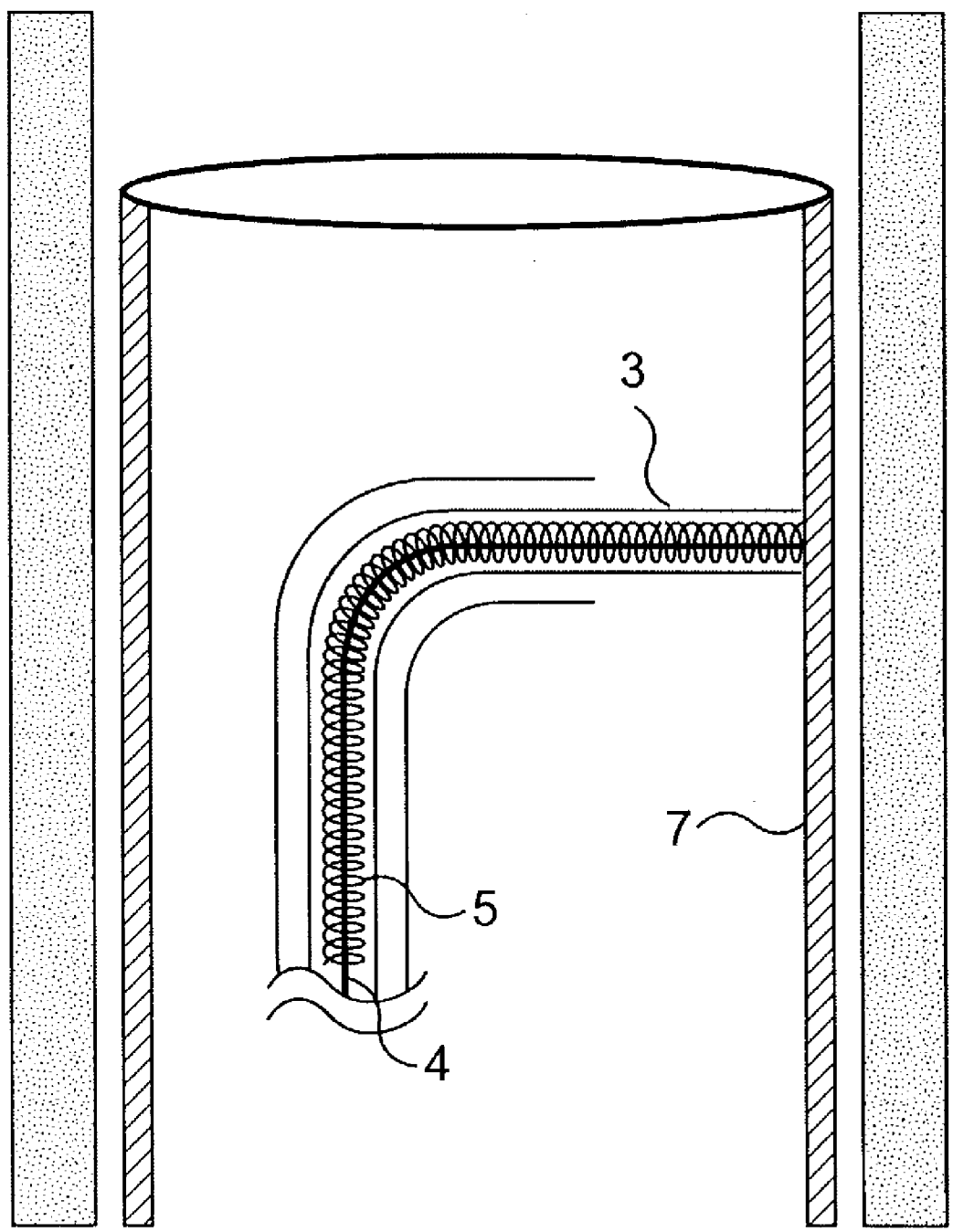
FIG. 6 is a perspective view of an inner sheath advanced from an outer sheath of a delivery catheter in accordance with an embodiment of the present invention.
Figure 7:
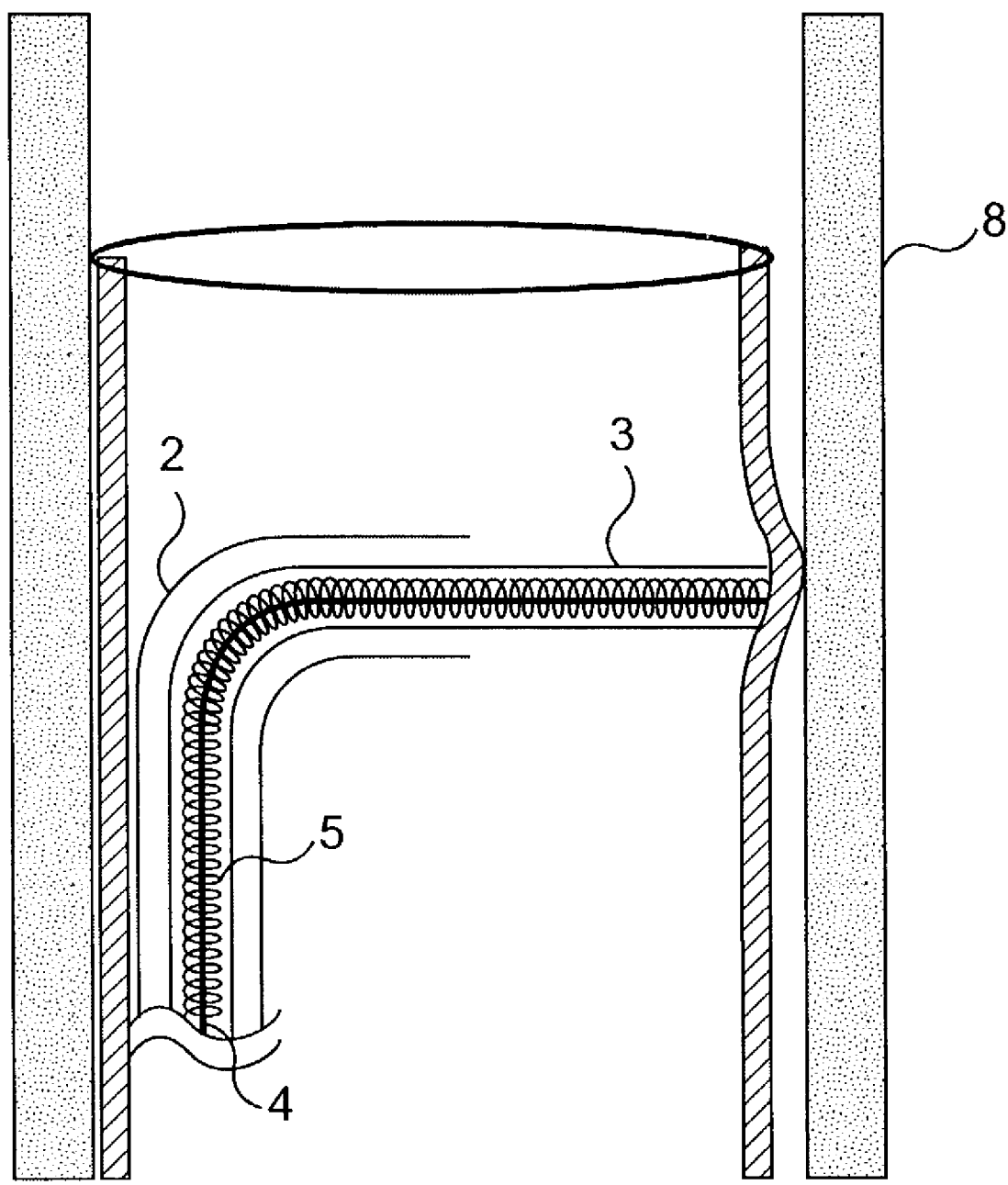
FIG. 7 is a perspective view of an inner sheath further advanced from an outer sheath of a delivery catheter in accordance with an embodiment of the present invention.

After the end portion assumes an angular configuration, the inner sheath 3 is advanced such that it extends to contact the surgical component 7, as shown in FIG. 6. The inner sheath 3 is further advanced such that the outer sheath 2 contacts the surgical component 7, or a vessel wall 8, at a location opposite where the inner sheath 3 has engaged the surgical component 7. The inner sheath 3 is still further advanced such that it applies pressure on the surgical component 7 to push the surgical component 7 against the vessel wall 8, as shown in FIG. 7. The laser fiber assembly 4, which is positioned within the inner sheath 3, is then activated. At least one fastener 5 is positioned within, around, or in conjunction with the laser fiber assembly 4. The laser fiber assembly 4 may comprise an optical fiber and a Ho:YAG laser, a Ho:YLF laser, a laser with a wavelength between 1.8 and 2.2μ or any other suitable fiber and laser combination.

Figure 8:
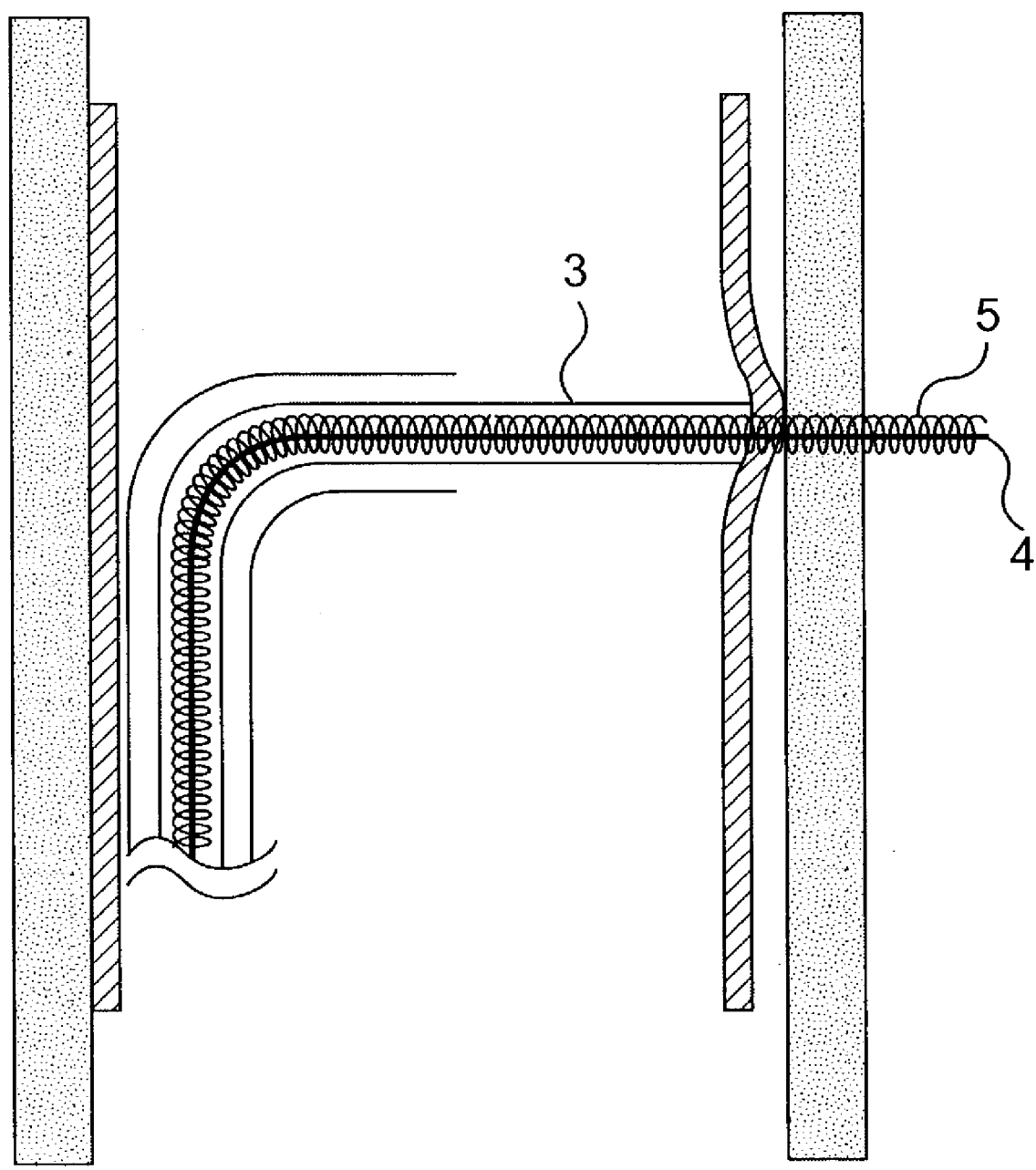
FIG. 8 is a perspective view of a laser fiber assembly advanced through a surgical component and a vessel wall in accordance with an embodiment of the present invention.
Figure 9:
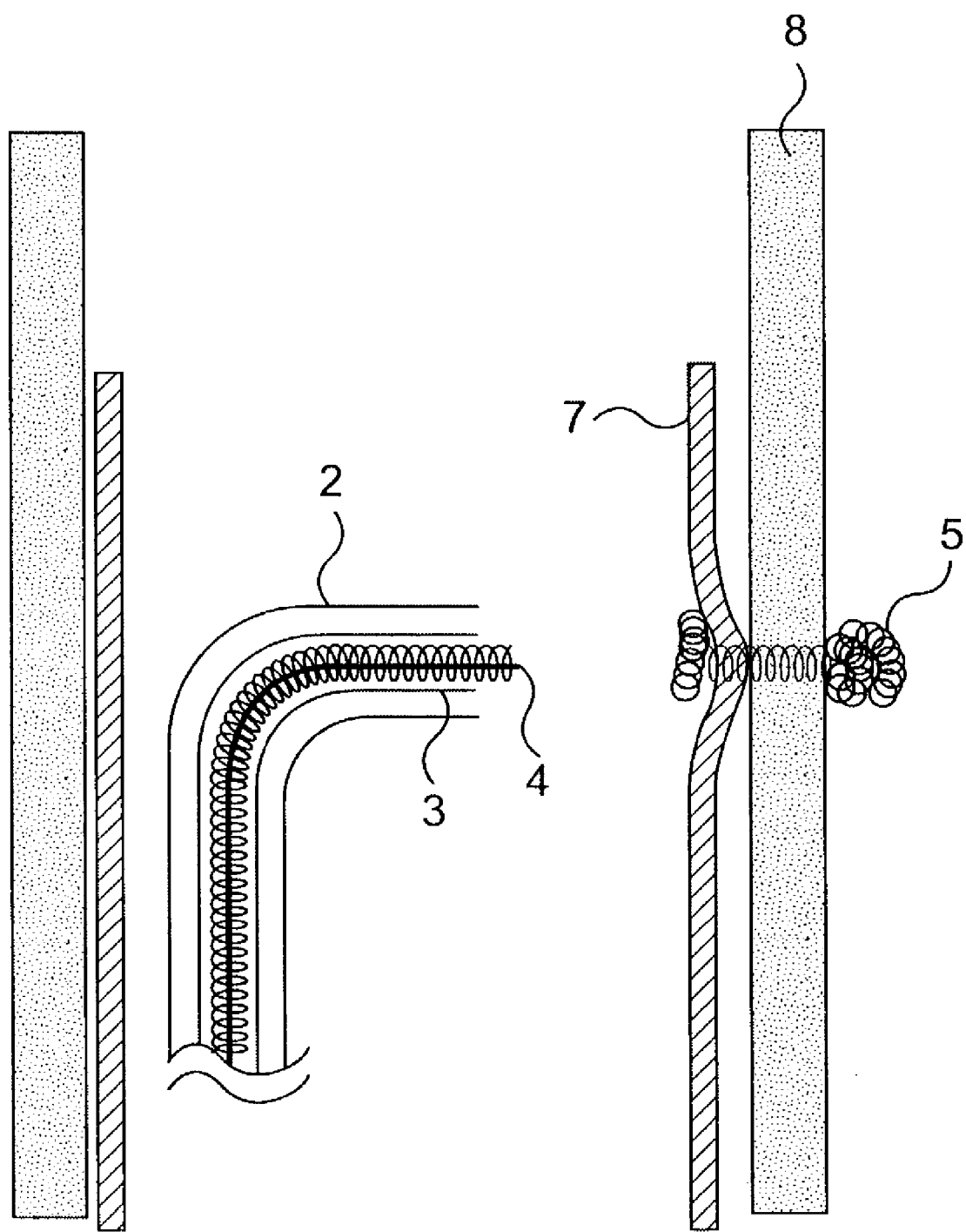
FIG. 9 is a perspective view of a laser fiber assembly and an inner sheath of a delivery catheter retracted through a treatment specific hole in a surgical component and a vessel in accordance with an embodiment of the present invention.

Once activated, the laser fiber assembly 4 and the fastener 5 are advanced through the surgical component 7 and the vessel wall 8 either simultaneously or sequentially to create a treatment specific hole in the surgical component 7 and the vessel wall 8, as depicted in FIG. 8. The fastener 5 extends through the treatment specific hole in the surgical component 7 and the vessel wall 8. As shown in FIG. 9, the laser fiber assembly 4 and inner sheath 3 are retracted inside the outer sheath 2, thereby deploying the fastener 5 to secure the surgical component 7 to the vessel wall 8. This method may be repeated at various locations of the procedure specific area to deploy multiple fasteners 5. This surgical procedure may be used to secure a material such as, but not limited to, a surgical component to surgical component, surgical component to vessel, or vessel to vessel.

Figure 10:
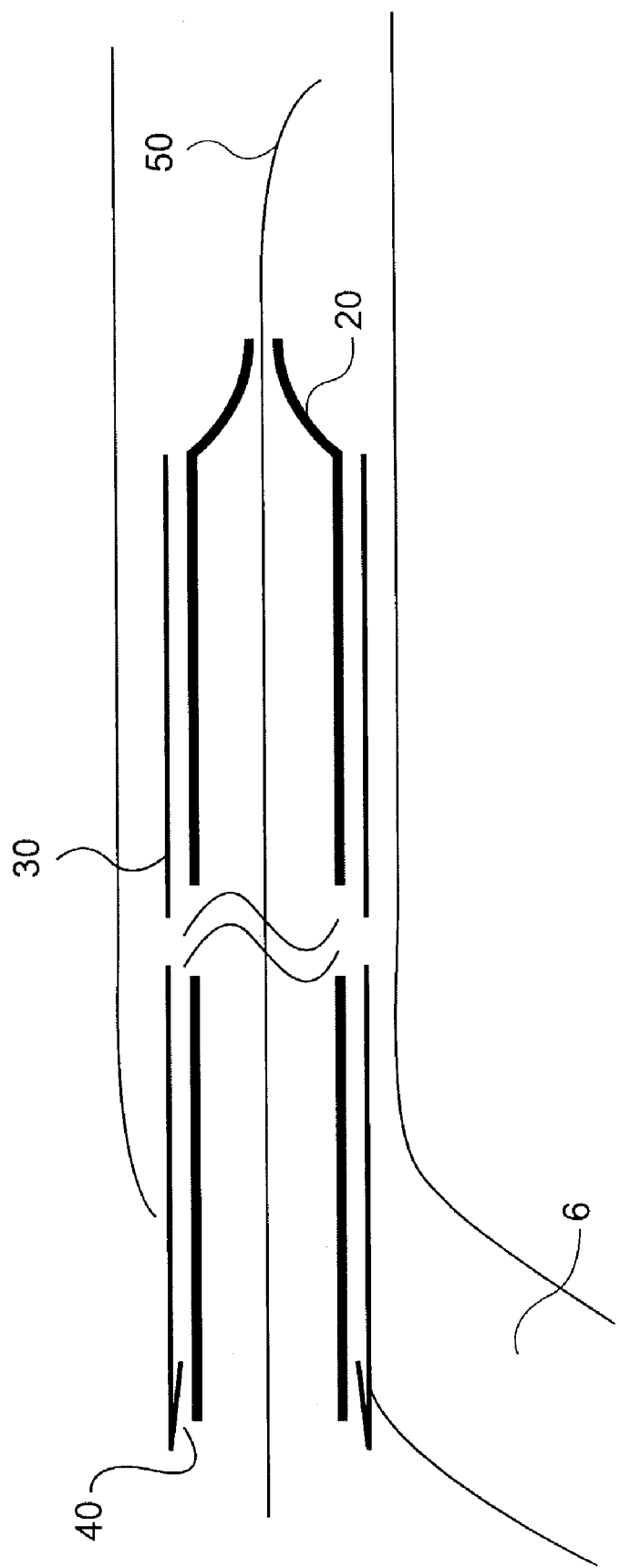
FIG. 10 is a perspective view of an introducer sheath inserted into a vessel over a guide wire in accordance with an embodiment of the present invention.
Figure 11:
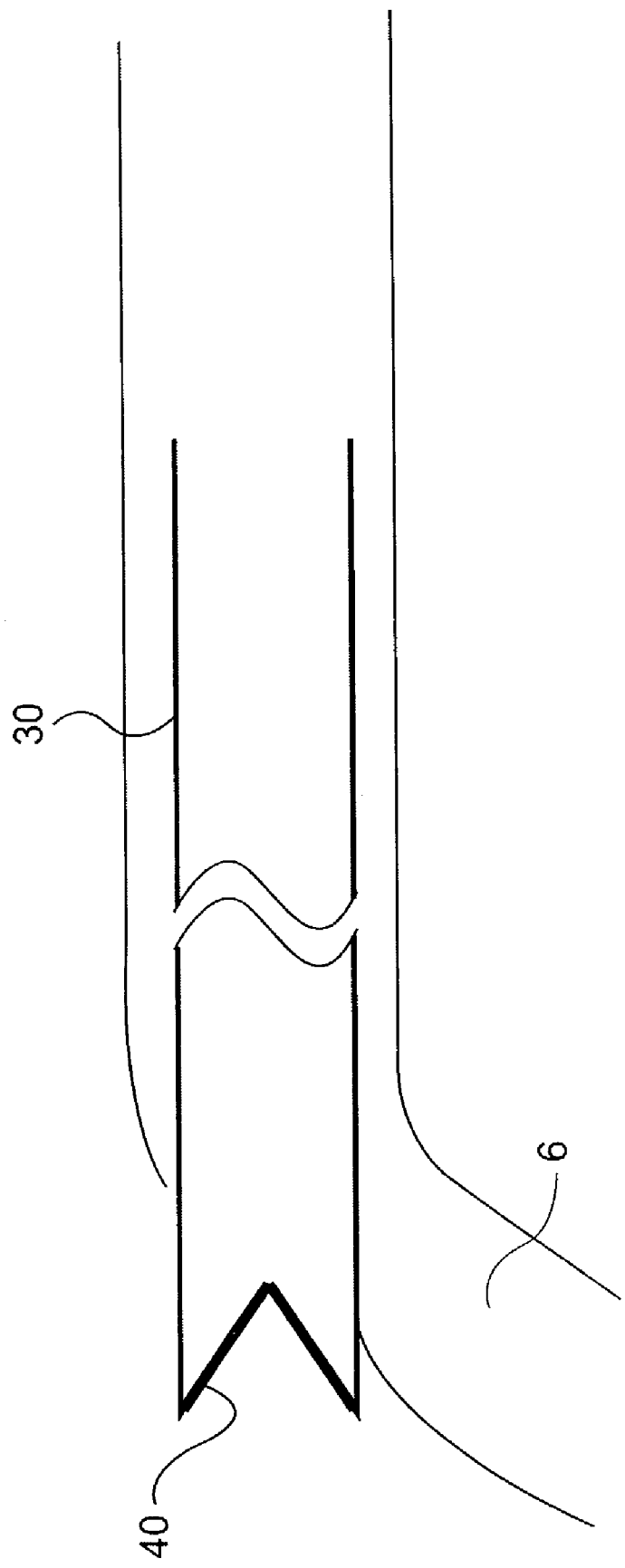
FIG. 11 is a perspective view of an introducer sheath advanced within a vessel in accordance with an embodiment of the present invention.
Figure 12:
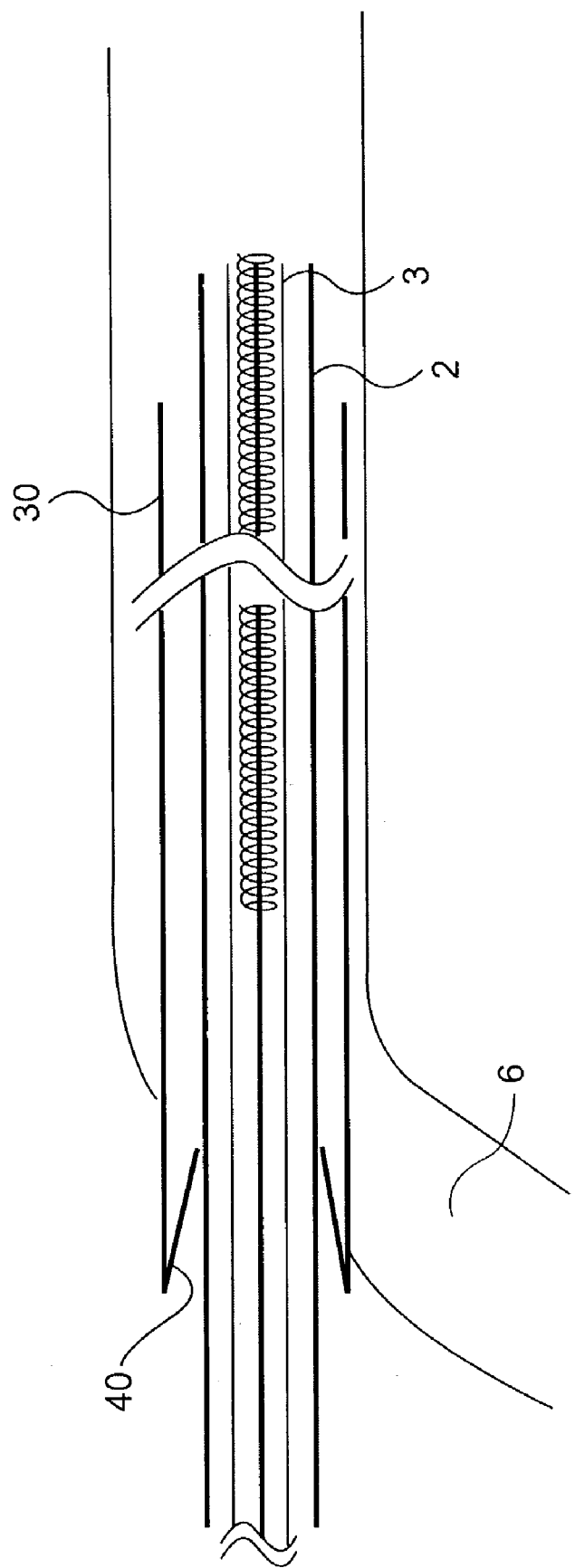
FIG. 12 is a perspective view of a delivery catheter advanced within a vessel through an introducer sheath in accordance with an embodiment of the present invention.

In an alternate embodiment of the present invention, the delivery catheter 1 depicted in FIGS. 1 through 9 may be inserted into a vessel through an introducer sheath 30, as shown in FIGS. 10 through 12. A needle may first be inserted into the vessel. A guide wire 50 may then be inserted into the needle and threaded into the vessel, allowing the needle to be removed. A dilator 20 may be used to make the opening into the vessel larger. The dilator 20 may be a tapered form, solid catheter with a center passageway through which the guide wire 50 traverses. After the opening is enlarged to the desired size, an introducer sheath 30 with the tapered dilator 20 located within it may be inserted over the guide wire 10, as shown in FIG. 10. Once the end of the introducer sheath 30 is in the desired position within the vessel, the dilator 20 and guide wire 10 are removed, so that the delivery catheter may be inserted. The delivery catheter 1 may be inserted into the introducer sheath 30 through a hemostatic valve 40 of the introducer sheath 30, shown in FIG. 11. The delivery catheter 1 may be advanced within the introducer sheath 30 until the distal end of the outer sheath 2 or the inner sheath 3 is within the vessel 6, rather than within the introducer sheath 30, as depicted in FIG. 12.

Figures 13A, 13B:
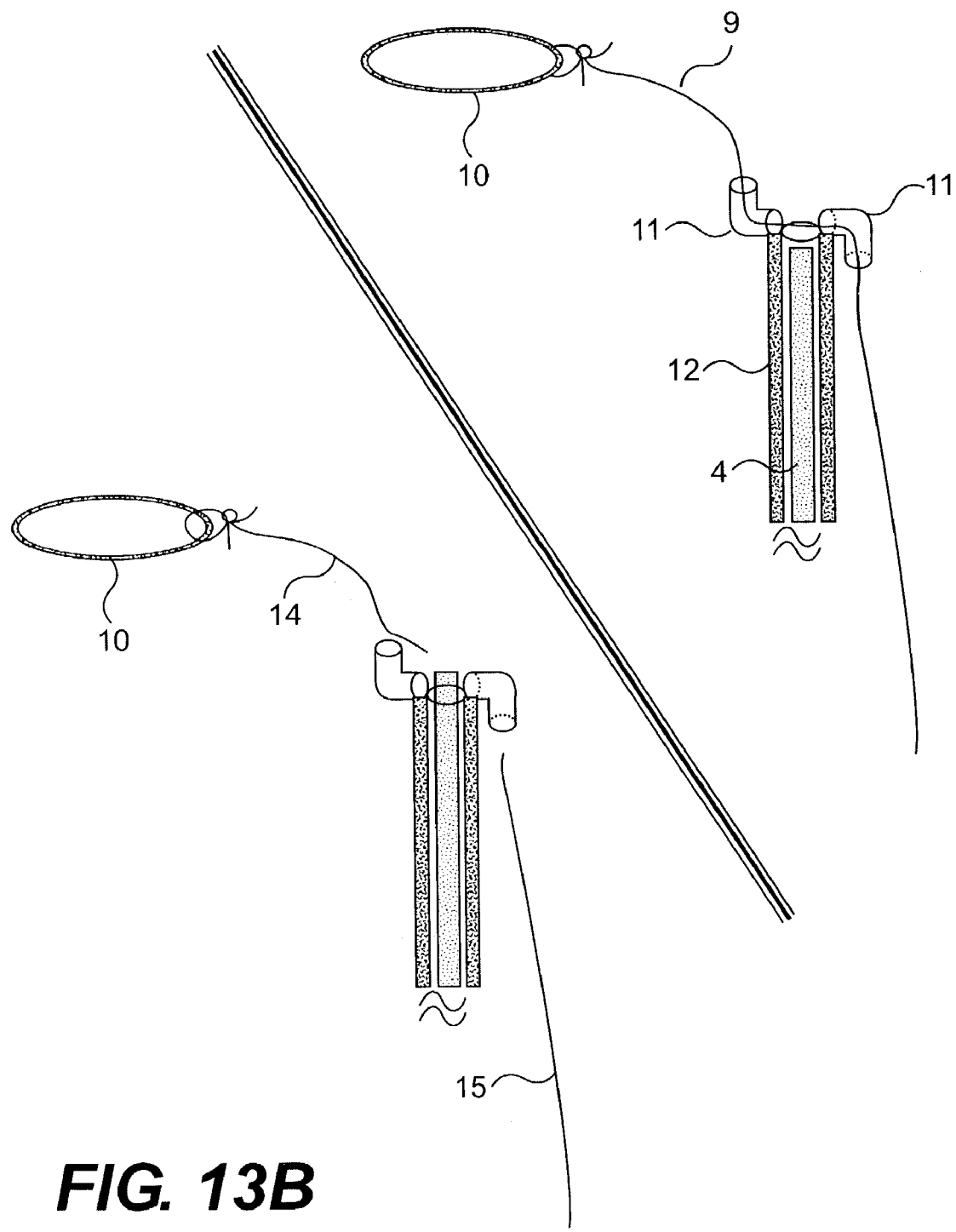
FIG. 13A is a perspective view of a suture threaded through a passageway in a distal end of a catheter in accordance with an embodiment of the present invention.
FIG. 13B is a perspective view of a laser fiber assembly advanced toward the suture of FIG. 13A for transecting the suture in accordance with an embodiment of the present invention.

In another alternate embodiment of the present invention, shown in FIGS. 13A and B, the method of transecting a suture comprises the steps of threading a suture 9 through a passageway 11 at the distal end 12 of a catheter 1, wherein the distal end 12 contains a laser fiber assembly 4, as shown in FIG. 13A, activating the laser fiber assembly 4, and advancing the laser fiber assembly 4 toward the passageway 11 to transect the suture 9 into two pieces 14 and 15, as shown in FIG. 13B. The suture 9 may be attached to a fixed material 10, such as, but not limited to, tissue or prosthetic material, as depicted in FIGS. 13A and B.

It will be apparent to those skilled in the art that variations and modifications of an embodiment of the present invention can be made without departing from the scope or spirit of the invention. For example, the method of performing a surgical procedure could be used in settings other than the repair of aneurysms. The method could be used to attach any surgical component, such as, but not limited to, a prosthetic material to any tissue, to another surgical component, or tissue to tissue with a metal or plastic attachment device, such as a shape memory metal, plastic staple, or metal staple or any other suitable fastener or material. For instance, the method could be used to attach a prosthetic mesh to fascia through a laparoscope/endoscope or directly in an open operation for hernia repair. Thus, it is intended that an embodiment of the present invention cover all such modifications and variations of the invention, provided they come within the scope of the appended claims and their equivalents.

What is claimed is:

1. A method of performing a surgical procedure, comprising the steps of:
   advancing a delivery catheter, at least one fastener, and at least one material to a procedure specific area;
   activating a laser fiber assembly disposed within the delivery catheter, wherein the at least one fastener is positioned at the distal portion of the laser fiber assembly;
   advancing the laser fiber assembly and the at least one fastener through the at least one material at the procedure specific area to create a treatment specific hole in the at least one material; and
   retracting the laser fiber assembly such that the at least one fastener remains inserted in the at least one material.

2. The method according to claim 1, wherein the laser fiber assembly further comprises a Ho:YAG laser.

3. The method according to claim 1, further comprising the step of articulating the delivery catheter, prior to activating the laser fiber assembly, wherein a distal portion of the delivery catheter assumes an angular configuration.

4. The method according to claim 1, wherein the delivery catheter further comprises an inner sheath.

5. A method of performing a surgical procedure, comprising the steps of:
   advancing a delivery catheter, at least one fastener, and a surgical component through a vessel to a procedure specific area within the vessel;
   activating a laser fiber assembly disposed within the delivery catheter, wherein the at least one fastener is positioned at a distal portion of the laser fiber assembly;
   advancing the laser fiber assembly and the fastener through a the surgical component and the vessel to create a treatment specific hole in the surgical component and the vessel through which the fastener extends; and
   retracting the laser fiber assembly such that the at least one fastener remains attached to the surgical component and the vessel.

6. The method according to claim 5, wherein the laser fiber assembly further comprises a Ho:YAG laser.

7. The method according to claim 5, further comprising the step of extending an inner sheath disposed within the delivery catheter, prior to activating the laser fiber assembly, wherein a distal portion of the inner sheath assumes an angular configuration.

8. The method according to claim 5, wherein the laser fiber assembly is advanced before the at least one fastener is advanced.

9. A method of performing a surgical procedure, comprising the steps of:
   advancing a delivery catheter and a surgical component through a vessel to a procedure specific area within a vessel;
   extending the delivery catheter such that an inner sheath of the delivery catheter extends from the delivery catheter, wherein an end portion of the inner sheath assumes an angular configuration;
   advancing the inner sheath from within the delivery catheter such that the delivery catheter contacts a the surgical component at a location opposite to a point of contact of the inner sheath;
   further advancing the inner sheath such that the inner sheath contacts the surgical component;
   activating a laser fiber assembly disposed within the inner sheath, wherein at least one fastener is positioned at a distal portion of the laser fiber assembly;
   advancing the laser fiber assembly and the at least one fastener through the surgical component and the vessel to create a treatment specific hole in the surgical component and the vessel through which the fastener extends; and
   retracting the laser fiber assembly and the inner sheath such that the at least one fastener remains attached to the surgical component and the vessel.

10. The method according to claim 9, wherein the laser fiber assembly further comprises a Ho:YAG laser.

11. The method according to claim 9, wherein the laser fiber assembly is advanced before the at least one fastener is advanced through the surgical component and the vessel.

* * * * *